(12) United States Patent
Urano et al.

(10) Patent No.: US 8,637,274 B2
(45) Date of Patent: Jan. 28, 2014

(54) INHIBITOR FOR THE FORMATION OF GAMMA-SECRETASE COMPLEX

(75) Inventors: Yasuomi Urano, Tokyo (JP); Takao Hamakubo, Tokyo (JP); Tatsuhiko Kodama, Tokyo (JP)

(73) Assignees: Kowa Company, Ltd., Nagoya-shi, Aichi (JP); Nissan Chemical Industries, Ltd., Tokyo (JP)

( * ) Notice: Subject to any disclaimer, the term of this patent is extended or adjusted under 35 U.S.C. 154(b) by 556 days.

(21) Appl. No.: 12/606,792

(22) Filed: Oct. 27, 2009

(65) Prior Publication Data
US 2010/0093010 A1    Apr. 15, 2010

Related U.S. Application Data

(63) Continuation of application No. 10/584,415, filed as application No. PCT/JP2004/019628 on Dec. 28, 2004, now abandoned.

(60) Provisional application No. 60/532,923, filed on Dec. 30, 2003.

(51) Int. Cl.
   *C12N 15/09*   (2006.01)

(52) U.S. Cl.
   USPC ............................................. 435/69.2; 435/4

(58) Field of Classification Search
   USPC .................................................. 435/4, 69.2
   See application file for complete search history.

(56) References Cited

U.S. PATENT DOCUMENTS

| | | | |
|---|---|---|---|
| 3,983,140 | A | 9/1976 | Endo et al. |
| 4,231,938 | A | 11/1980 | Monaghan et al. |
| 4,346,227 | A | 8/1982 | Terahara et al. |
| 4,444,784 | A | 4/1984 | Hoffman et al. |
| 5,177,080 | A | 1/1993 | Angerbauer et al. |
| 5,260,440 | A | 11/1993 | Hirai et al. |
| 5,273,995 | A | 12/1993 | Roth |
| 5,354,772 | A | 10/1994 | Kathawala |
| 5,856,336 | A | 1/1999 | Fujikawa et al. |
| 6,080,778 | A | 6/2000 | Yankner et al. |
| 6,440,387 | B1 | 8/2002 | Yankner et al. |
| 6,472,421 | B1 | 10/2002 | Wolozin |
| 6,620,821 | B2 | 9/2003 | Robl et al. |
| 6,627,409 | B2 | 9/2003 | Hook |
| 6,864,290 | B2 | 3/2005 | Schostarez et al. |
| 2002/0061901 | A1 | 5/2002 | Robl et al. |
| 2002/0072050 | A1 | 6/2002 | Hook |
| 2002/0107173 | A1 | 8/2002 | Friedhoff et al. |
| 2003/0083356 | A1 | 5/2003 | Schostarez et al. |
| 2004/0063634 | A1 | 4/2004 | Carr et al. |
| 2004/0087630 | A1 | 5/2004 | Allison et al. |
| 2005/0107461 | A1 | 5/2005 | Cai et al. |

FOREIGN PATENT DOCUMENTS

| | | |
|---|---|---|
| WO | 99/48488 A2 | 9/1999 |
| WO | 00/28981 A2 | 5/2000 |
| WO | 01/32161 A2 | 5/2001 |
| WO | 01/96311 A2 | 12/2001 |
| WO | 02/15892 A2 | 2/2002 |
| WO | 02/062824 A2 | 8/2002 |
| WO | 02/062842 A1 | 8/2002 |
| WO | 03/077896 A1 | 9/2003 |

OTHER PUBLICATIONS

Gu et al. "APH-1 interacts with mature and immature forms of presenilins and nicastrin and may play a role in maturation of presenilin.micastrin complexes", JBC, 2003, 278(9):7374-7380.*
Capell et al. "The proteolytic fragments of the Alzheimer's disease-associated presenilin-1 form heterodimers and occur as a 100-150-kDa molecular mass complex", JBC, 1998, 273(6):3205-3211.*
Parkin et al. "Characterization of detergent-insoluble complexes containing the familial Alzheimer's disease-associated presenilins", J. Neurochem. 1999, 72:1534-1543.*
Kim et al. "Subcellular localization of presenilins: association with a unique membrane pool in cultured cells", Neurobiology of Disease, 2000, 7:99-117.*
Wolfe et al. "Peptidomimetic probes and molecular modeling suggest that Alzheimer's gamma-secretase is an intramembrane-cleaving aspartyl protease", Biochemistry, 1999, 38:4720-4727.*
Van Gassen et al. "Amyloid, presenilins, and Alzheimer's disease", The Neuroseicntist, 2003, 9(2):117-126.*
Yamashita, H. et al., Bunshi Nokekkanbyo, Oct. 1, 2004, pp. 415-425, vol. 3, No. 4.
Simons, M., et al., "Cholesterol depletion inhibits the generation of β-amyloid in hippocampal neurons", Proc. Natl. Acad. Sci., USA, May 1998, pp. 6460-6464, vol. 95.
Kojro, E. et al., "Low cholesterol stimulates the nonamyloidogenic pathway by its effect on the α-secretase ADAM 10", Proc. Natl. Acad. Sci., USA, 2001, pp. 5815-5820, vol. 98, No. 10.
Wolozin, B., "Cholesterol and Alzheimer's disease", Biochemical Society Transaction, 2002, pp. 525-529, vol. 30, part. 4.
Wahrle, S., et al., "Cholesterol-Dependent γ-Secretase Activity in Buoyant Cholesterol-Rich Membrane Microdomains", Neurobiology of Disease, 2002, pp. 11-23, vol. 9, No. 1.

(Continued)

*Primary Examiner* — Bin Shen
(74) *Attorney, Agent, or Firm* — Westerman, Hattori, Daniels & Adrian, LLP

(57) ABSTRACT

It is intended to provide an inhibitor for the formation of a γ-secretase complex which comprises a cholesterol synthesis inhibitor or a protein geranylgeranylation regulator as the active ingredient; and use of a cholesterol synthesis inhibitor or a protein geranylgeranylation regulator for producing the same. It is also intended to provide a method of screening a substance having an effect of inhibiting the formation of an active complex of γ-secretase which comprises assaying the activity of inhibiting cholesterol synthesis or quantifying cholesterol accumulated in lipid rafts in cells. It is also intended to provide a method of screening a cholesterol synthesis inhibitor, a protein geranylgeranylation regulator or an HMG-CoA reductase inhibitor which comprises assaying the effect of inhibiting the formation of an active complex of γ-secretase. Moreover, it is intended to provide a method of screening an effect of a test substance on γ-secretase which comprises measuring the distribution of constituents (nicastrin, APH-1, Pen-2 and so on) required by γ-secretase for the formation of its active complex in cells.

5 Claims, 4 Drawing Sheets

(56) References Cited

OTHER PUBLICATIONS

Wada, S. et al., "γ-Secretase Activity is Present in Rafts but Is Not Cholesterol-Dependent", Biochemistry, 2003, pp. 13977-13986, vol. 42, No. 47.

T. Yamazaki, "P3-F-17", Clinical Neurology, Dec. 2002, p. 1309, vol. 42, No. 12.

International Search Report of PCT/JP2004/019628, date of mailing May 10, 2005.

Translation of International Preliminary Report on Patentability mailed Aug. 31, 2006, of International Application No. PCT/ JP2004/ 019628.

Nussbaum, M.D., Robert L. et al., "Alzheimer's Disease and Parkinson's Disease", The New England Journal of Medicine, Apr. 3, 2003, p. 1356-1364.

Simons, Kai et al., "Cholesterol, lipid rafts, and disease", The journal of Clinical Investigation, Sep. 2002, p. 597-603, vol. 110.

Rothblat, George H., et al., "Cell cholesterol efflux: integration of old and new observations provides new insights", Journal of Lipid Research, 1999, p. 781-796, vol. 40.

Tedde, Andrea, et al., "Identification of New Presenilin Gene Mutations in Early-Onset Familial Alzhemer Disease", Arch Neurol, Nov. 2003, p. 1541-1544, vol. 60.

Roberts, Susan B., "γ-Secretase inhibitors and Alzheimer's disease", Advanced Drug Delivery Reviews, 2002, pp. 1579-1588, vol. 54.

Micchelli, Craig A., et al., "γ-Secretase / presenilin inhibitors for Alzheimer's disease phenocopy Notch mutations in *Drosophila*", The FASEB Journal, Jan. 2003, pp. 79-81, vol. 17.

Takahashi, Yasuko, et al., "Sulindac Sulfide Is a Noncompetitive γ-Secretase Inhibitor That Preferentially Reduces Aβ42 Generation", The Journal of Biological Chemistry, May 16, 2003, pp. 18664-18670, vol. 278, No. 20.

Weggen, Sascha, et al., "Aβ42-lowering Nonsteroidal Anti-inflammatory Drugs Preserve Intramembrane Cleavage if the Amyloid Precursor Protein (APP) and ErbB-4 Receptor Signaling through the APP intracellular Domain", The Journal of Biological Chemistry, Aug. 15, 2003, pp. 30748-30754, vol. 278, No. 33.

Zhou, Yan, et al., "Nonsteroidal Anti-Inflammatory Drugs Can Lower Amyloidogenic Aβ42 by Inhibition Rho", Science, Nov. 14, 2003, pp. 1215-1217, vol. 302.

Greenspan, Michael D., et al., "Inhibition of hydroxymethylglutaryl-coenzyme A synthase by L-659,699", Proc. Natl. Acad. Sci. USA, 1987, pp. 7488-7492, vol. 84.

Hemingway, Cheryl J. et al., "Gemfibrozil activation of AMP-activated protein kinase", S676 Biochemical Society Transactions, 1997, p. 2.

Van Beek, Edmond, "Farnesyl Pyrophosphate Synthase Is the Molecular Target of Nitrogen-Containing Bisphosphonates", Biochemical and Biophysical Research Communications, 1999, pp. 108-111, vol. 264.

Sakurai, Takashi, et al., "Amyloid precursor protein and lipid rafts", 2003, pp. 291-296, vol. 54, No. 4.

Supplementary European Search Report dated Oct. 30, 2007, issued in corresponding European patent application No. 04 80 7983.

Abraham Fisher et al., "M1 Muscarinic Agonists Can Modulate Some of the Hallmarks in Alzheimer's Disease: Implications in Future Therapy", Journal of Molecular Neuroscience, Birkhaeuser, Cambridge, MA, USA, Aug. 2003, pp. 349-356, vol. 20, No. 3.

Office Action issued Jul. 17, 2009 in corresponding European Patent application 04 807 983.

Fassbender, K., et al., "Simvastatin strongly reduces levels of Alzheimer's disease β-amyloid peptides Aβ42 and Aβ40 in vitro and in vivo," PNAS, May 8, 2001, pp. 5856-5861, vol. 98, No. 10.

Wolozin, B., M.D., et al., "Decreased Prevalence of Alzheimer Disease Associated With 3-Hydroxy-3-Methyglutaryl Coenzyme A Reductase Inhibitors"; Arch Neurol, vol. 57, pp. 1439-1443, Oct. 2000.

* cited by examiner

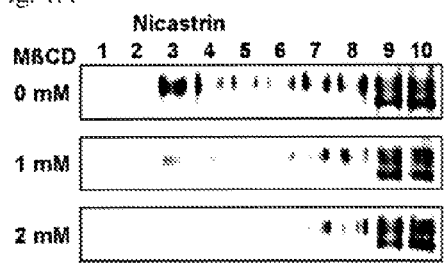
Fig. 1A Nicastrin
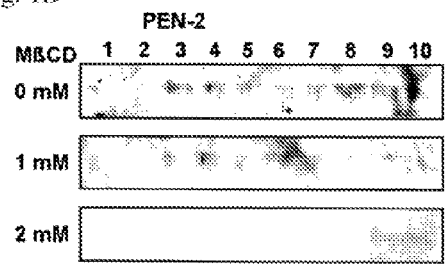
Fig. 1D PEN-2
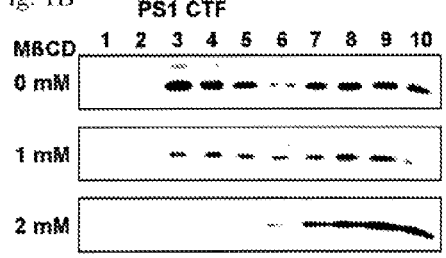
Fig. 1B PS1 CTF
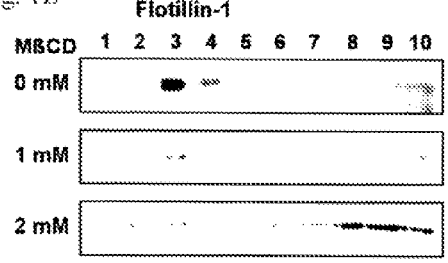
Fig. 1E Flotillin-1
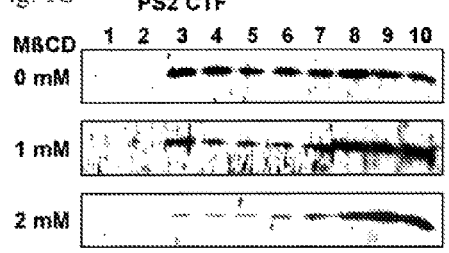
Fig. 1C PS2 CTF
DMEM +0~2 mM MβCD, 37°C, 30min incubation

INHIBITOR FOR THE FORMATION OF GAMMA-SECRETASE COMPLEX

RELATED APPLICATION

This application is a continuation application of U.S. patent application Ser. No. 10/584,415 filed on Jun. 26, 2006, now abandoned, which is a National Stage Application of PCT/JP04/19628 filed Dec. 28, 2004, which is hereby incorporated by reference in its entirety, which claims priority to provisional application 60/532,923 filed on Dec. 30, 2003.

TECHNICAL FIELD

The present invention relates to an inhibitor for the formation of a γ-secretase complex or agent for decreasing the distribution of active complex of γ-secretase in lipid rafts comprising a cholesterol synthesis inhibitor or a protein geranylgeranylation regulator as the active ingredient. The present invention also relates to a method of screening a substance having an effect of inhibiting the formation of an active complex of γ-secretase or a method of screening a substance having an effect of decreasing the distribution of γ-secretase in lipid rafts comprising assaying an activity of inhibiting cholesterol synthesis or quantifying cholesterol accumulated in lipid rafts in cells. The present invention also relates to a method of screening a cholesterol synthesis inhibitor, a protein geranylgeranylation regulator or an HMG-CoA reductase inhibitor comprising assaying an effect of inhibiting the formation of an active complex of γ-secretase. The present invention further relates to a method of inhibiting the formation of an active complex of γ-secretase or a method of decreasing the distribution of active complex of γ-secretase in lipid rafts using a cholesterol synthesis inhibitor or a protein geranylgeranylation regulator. The present invention further relates to use of a cholesterol synthesis inhibitor or a protein geranylgeranylation regulator for producing an inhibitor for the formation of a γ-secretase complex or an agent for decreasing the distribution of active complex of γ-secretase in lipid rafts. Moreover, the present invention relates to a method of screening an effect of a test substance on γ-secretase comprising measuring the distribution of the constituents such as nicastrin, APH-1 and Pen-2 required by γ-secretase for the formation of an active complex in cells.

BACKGROUND ART

Alzheimer disease (AD) which is a representative disease of senile dementia is a degenerative disease characterized by atrophy of brain, deposition of senile plaque and formation of neurofibril, and neuronal loss is considered to induce the dementia symptom (N. Eng. J. Med. 2003; 348:1356). In AD, an amyloid precursor protein (APP) which is a single transmembrane protein is cleaved at an extracellular part thereof by β-secretase in lipid rafts (cell membrane microdomain where sphingolipid and cholesterol are integrated) rather than by α-secretase in cell membrane, and further, the transmembrane part of the molecule is cleaved by γ-secretase to produce Aβ40 and Aβ42. Above all, deposition of the Aβ42 peptide which has highly cohesive property in the brain causes neuronal loss and leads to atrophy of the brain. In contrast to the β-secretase of single transmembrane protein, the γ-secretase is considered to be a complex composed by association of an active subunit of presenilin with nicastrin, APH-1 and Pen-2 (SEITAI NO KAGAKU 2003; 291-296), and to be involved in the production of Aβ40 and Aβ42 in lipid rafts. It has been reported that the cholesterol level may affect the secretase activity, for instance, increased level of cholesterol decreases the α-secretase activity but increases the β-secretase activity, while the γ-secretase activity is not largely affected (Biochem. Soc. Transact. 2002; 30: 525-529). With respect to the γ-secretase activity after removal of cholesterol from the lipid raft using a cholesterol inclusion compound (J. Lipid Res. 1999; 40: 781-796), there are two different findings; one paper reported disappearance of the γ-secretase activity (Neurobiol. Res. 2002; 30: 525-529); and the other paper reported no influence on the γ-secretase activity (Biochemistry 2003; 42: 13977-13986).

Biosynthetic process of cholesterol is initiated by a step of the formation of mevalonic acid from 3-hydroxy-3-methylglutaryl-CoA (HMG-CoA) by a HMG-CoA reductase, where the HMG-CoA is produced from acetyl-CoA by a HMG-CoA synthetase. The resultant mevalonic acid is converted to isopentenyl pyrophosphate referred to as an active isoprene unit, and then converted through geranyl pyrophosphate to farnesyl pyrophosphate by a farnesyl pyrophosphate synthetase. Subsequently, farnesyl pyrophosphate is converted to squalene by a squalene synthetase, then to 2,3-epoxysqualene by a squalene epoxidase. Thereafter, 2,3-epoxysqualene is converted to lanosterol by a lanosterol synthetase to form a basic structure of cholesterol, and finally cholesterol is produced through various modification reactions.

A part of farnesyl pyrophosphate formed by a farnesyl pyrophosphate synthetase reacts with isopentenyl pyrophosphate to form geranylgeranyl pyrophosphate, which is used for geranylgeranylation of proteins such as Rho and Rac by an action of a geranylgeranyl transferase.

Also, as AMPK inactivates the HMG-CoA reductase by phosphorylation, an AMPK activating agent may exert the similar effect as HMG-CoA reductase inhibitor. Furthermore, the AMPK also has an effect to phosphorylate and inactivate an acetyl-CoA carboxylase, so that synthesis of fatty acid is suppressed accordingly. Also, it has been known that fibrate also has an action to inhibit HMG-CoA reductase through activation of AMPK.

The inhibitor of HMG-CoA reductase is an agent to inhibit antagonistically the HMG-CoA reductase which catalyzes the conversion of HMG-CoA into mevalonic acid at a rate-limiting step of cholesterol biosynthesis, and has been known as a therapeutic agent for hypercholesteremia. A retrospective epidemiological study has demonstrated that a patient who takes the HMG-CoA reductase inhibitor shows a low AD prevalence rate (Arch. Neurol. 2000; 57: 1439-1433) and also that the HMG-CoA reductase inhibitor decreases the formation of Aβ peptide in vitro and in vivo. Based on the above findings, the usefulness of the HMG-CoA reductase inhibitor for the treatment of AD has been applied for patents (WO 02/062824, WO 01/096311, WO 01/32161, WO 00/28981, WO 99/48488, U.S. Pat. Nos. 6,472,421, 6,440,387, 6,080, 778). In the specifications of these patents, it has been described a possibility of the HMG-CoA reductase inhibitor to decrease the production of Aβ peptide through processing of APP, namely through controlling secretase activity, however, there is no description about the decrease of γ-secretase activity.

There has currently been an active study on γ-secretase inhibitor as a therapeutic agent for AD (Adv. Drug Deliv. Rev. 2002; 54: 1579-1588) from the reasons such as the γ-secretase is an enzyme to produce Aβ42 peptide, and that genetic mutation of presenilin which is an active subunit of the enzyme can be the cause of AD (Arch. Neurol. 2003; 60: 1541-1544). However, the γ-secretase cleaves not only APP but also Notch, ErbB4, CD44, LRP and the like, and the enzyme with high potency may cause adverse reaction (FASEB J. 2003; 17: 79-81), therefore, development of γ-secretase inhibitor has not always progressed successfully. In the existing drugs, it has been reported that some nonsteroidal antiinflammatory drug having inhibitory activity for γ-secretase specifically blocked the production of Aβ42 without inhibiting the cleavage of Notch (J. Biol. Chem. 2003; 278:30748-30754, J. Biol. Chem. 2003; 278: 18664-18670). With respect to a mechanism of action of the drug, involvement of Rho suppression has been suggested (Science 2003; 302: 1215-1217).

DISCLOSURE OF THE INVENTION

The present inventors have investigated using the sucrose density-gradient method an amount of γ-secretase complex in lipid rafts in nerve cell where productions of Aβ40 and Aβ42 are supposed to take place, and surprisingly found that a quantity of γ-secretase complex existing in lipid rafts and an activity thereof were decreased depending on a remaining amount of cholesterol in the lipid rafts, not only by the cholesterol inclusion compounds such as methyl-β-cyclodextrin which removes cholesterol from lipid rafts and destroy the structure thereof, but also by an inhibitor of cholesterol synthesis which depresses an amount of cholesterol in the lipid rafts, and have thus completed the present invention. In consequence, the present invention provides a new type of inhibitor for γ-secretase activity which decreases the distribution of γ-secretase complex in lipid rafts and a method of screening thereof.

In addition, the present inventors have found that screening of an effect of a test substance on γ-secretase can be performed by the procedure of adding the test substance in a cell culture and measuring the distribution of constituents such as nicastrin, APH-1 and Pen-2 required by γ-secretase for the formation of an active complex thereof in cells.

First aspect of the present invention is to provide a method of screening a substance having an effect of inhibiting the formation of an active complex of γ-secretase comprising assaying an activity of inhibiting cholesterol synthesis; in more detail, a method of screening a substance having an effect of inhibiting the formation of an active complex of γ-secretase comprising assaying an activity of inhibiting the synthesis of cholesterol to be accumulated in lipid rafts.

Second aspect of the present invention is to provide a method of screening a substance having an effect of decreasing the distribution of an active complex of γ-secretase in lipid rafts comprising assaying an activity of inhibiting cholesterol synthesis; in more detail, a method of screening a substance having an effect of decreasing the distribution of an active complex of γ-secretase in lipid rafts comprising assaying an activity of inhibiting the synthesis of cholesterol to be accumulated in lipid rafts.

Third aspect of the present invention is to provide a method of screening a substance having an effect of inhibiting the formation of an active complex of γ-secretase comprising measuring an amount of cholesterol accumulated in lipid rafts in cells by culturing the cell in the presence of the test substance.

Fourth aspect of the present invention is to provide a method of screening a substance having an effect of decreasing the distribution of γ-secretase in lipid rafts comprising measuring an amount of cholesterol accumulated in lipid rafts in cells by culturing the cell in the presence of the test substance.

Fifth aspect of the present invention is to provide a method of screening a cholesterol synthesis inhibitor, a protein geranylgeranylation regulator or an HMG-CoA reductase inhibitor comprising assaying an effect of inhibiting the formation of an active complex of γ-secretase; in more detail, a method of screening a cholesterol synthesis inhibitor, a protein geranylgeranylation regulator or an HMG-CoA reductase inhibitor comprising assaying an effect of inhibiting the formation of an active complex of γ-secretase in lipid rafts.

Sixth aspect of the present invention is to provide a method of screening a cholesterol synthesis inhibitor, a protein geranylgeranylation regulator or an HMG-CoA reductase inhibitor comprising assaying an effect of decreasing the distribution of γ-secretase in lipid rafts; in more detail, a method of screening a cholesterol synthesis inhibitor, a protein geranylgeranylation regulator or an HMG-CoA reductase inhibitor comprising assaying an effect of decreasing the distribution of γ-secretase in lipid rafts.

Seventh aspect of the present invention is to provide an inhibitor for the formation of a γ-secretase complex comprising a cholesterol synthesis inhibitor or a protein geranylgeranylation regulator as an active ingredient.

Eighth aspect of the present invention is to provide an agent for decreasing the distribution of an active complex of γ-secretase in lipid rafts comprising a cholesterol synthesis inhibitor or a protein geranylgeranylation regulator as an active ingredient.

Ninth aspect of the present invention is to provide a method of inhibiting the formation of an active complex of γ-secretase using a cholesterol synthesis inhibitor or a protein geranylgeranylation regulator.

Tenth aspect of the present invention is to provide a method of decreasing the distribution of an active complex of γ-secretase in lipid rafts using a cholesterol synthesis inhibitor or a protein geranylgeranylation regulator.

Eleventh aspect of the present invention is to provide use of a cholesterol synthesis inhibitor or a protein geranylgeranylation regulator for producing an inhibitor for the formation of a γ-secretase complex.

Twelfth aspect of the present invention is to provide use of a cholesterol synthesis inhibitor or a protein geranylgeranylation regulator for producing an agent for decreasing the distribution of an active complex of γ-secretase in lipid rafts.

Moreover, the present invention relates to a method of screening an effect of a test substance on γ-secretase, comprising measuring the distribution of constituents such as nicastrin, APH-1 and Pen-2 required by γ-secretase for the formation of an active complex in cells by culturing the cell in the presence of the test substance.

BRIEF DESCRIPTION OF THE DRAWINGS

FIG. 1 shows an immunoblotting of cell membrane fraction after treatment with methyl-β-cyclodextrin. FIG. 1A illustrates the results for nicastrin; FIG. 1B illustrates for PS1CTF; FIG. 1C illustrates for PS2CTF; FIG. 1D illustrates for PEN-2; and FIG. 1E illustrates for flotillin-1. Each drawing of immunoblotting corresponds to the methyl-β-cyclodextrin concentration of 0 mM, 1 mM and 2 mM, respectively, from the top. Numeric symbols 1 to 10 in the drawing indicate fraction numbers of the sucrose density-gradient centrifugation.

FIG. 3 shows an immunoblotting of cell membrane fraction after treatment with HMG-CoA reductase inhibitor.

DETAILED DESCRIPTION OF THE INVENTION

Figure 2:
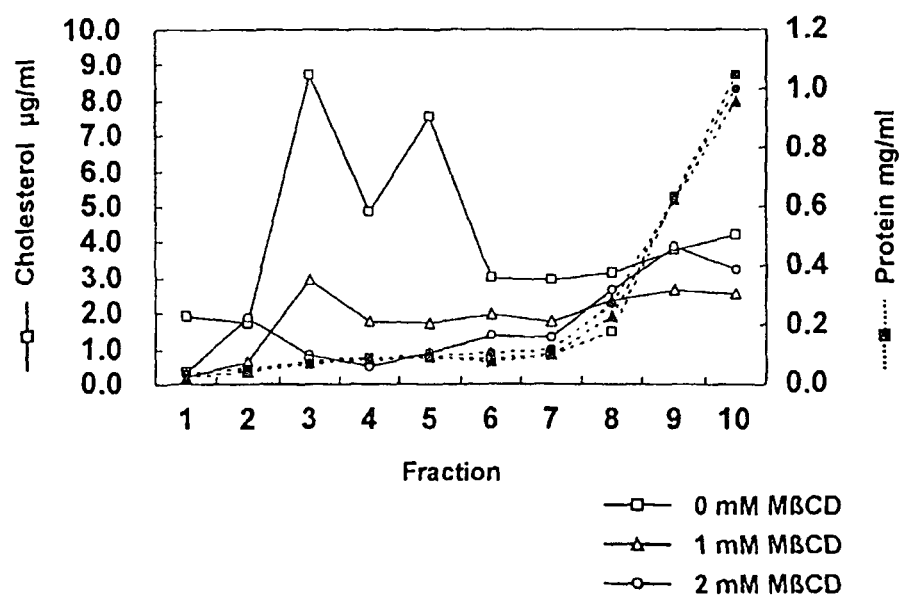
FIG. 2 shows a graph of changes of cholesterol and protein contents in the cell membrane fractions after treatment with methyl-β-cyclodextrin treatment. Square symbols (□ and ■) indicate the case when the methyl-β-cyclodextrin concentration is 0 mM; triangle symbols (Δ and ▲) indicate 1 mM; and circle symbols (○ and ●) indicate 2 mM. Outline symbols indicate cholesterol contents and black symbols indicate protein contents. The horizontal axis of the graph indicates fraction number, the vertical axis on the left hand indicates cholesterol concentration (μg/mL), and the vertical axis on the right hand indicates protein concentration (mg/mL).

As described later in Example, the present inventors have found that remarkable decrease of cholesterol content in lipid rafts is observed when the HMG-CoA reductase inhibitor is added to cell (refer to FIG. 3), and further, disappearance of the constituents of active complex of γ-secretase such as nicastrin, presenilin-1 and presenilin-2 from lipid rafts fraction (fraction No. 3) is observed (refer to FIG. 3A, FIG. 3B and FIG. 3C) as similarly observed when methyl-β-cyclodextrin is added. In the case of addition of the HMG-CoA reductase inhibitor, flotillin still remains in the lipid rafts fraction indicating that the structure of lipid rafts is maintained.

This finding is a clear demonstration that the cholesterol synthesis inhibitor which reduces the cholesterol content in the lipid rafts decreases the amount of active complex of γ-secretase in the lipid rafts depending on the remaining amount of cholesterol, and as the result, decreases the activity thereof. Further, from the fact that the suppression of Aβ production by NSAIDs is effected through Rho regulation (Science 2003; 302:1215-1217), and also from the fact that the HMG-CoA reductase inhibitor used in this experiment has an inhibitory activity not only for the cholesterol synthesis but also for the protein geranylgeranylation, it can be concluded that the HMG-CoA reductase inhibitor encompasses a function of a Rho geranylgeranilation inhibitor.

Furthermore, the present inventors have established a method for analyzing the distribution of constituents of an active complex of γ-secretase in cells such as nicastrin, presenilin-1 (PS1) and presenilin-2 (PS2) by fractionating the cell components using the sucrose density-gradient method and have demonstrated that the screening of a substance affecting on the activity of γ-secretase can be carried out by measuring the distribution of such constituents.

In the present invention, the cholesterol synthesis inhibitor is an agent capable of inhibiting cholesterol synthesis in vivo which may inhibit one or more steps in the pathway of the cholesterol biosynthesis in vivo. The cholesterol synthesis inhibitor of the present invention includes, for example, an HMG-CoA synthetase inhibitor (Proc. Natl. Acad. Sci. USA. 1987; 84: 7488-7492), an HMG-CoA reductase inhibitor, a squalene synthetase inhibitor, a squalene epoxidase inhibitor, a lanosterol synthetase inhibitor, an AMPK activator such as a fibrate (Biochemical Society Transactions 1997; 25: S676), and a farnesyl pyrophosphate synthetase inhibitor such as bisphosphonate (Biochem. Biophys. Res. Commun. 1999; 264: 108-111). Preferable cholesterol synthesis inhibitor includes an HMG-CoA reductase inhibitor.

The protein geranylgeranylation regulator of the present invention may be an agent capable of inhibiting or suppressing the formation of a geranylgeranylated protein in vivo which may inhibit or suppress one or more steps in the pathway of the geranylgeranylated protein synthesis in vivo. The protein geranylgeranylation regulator of the present invention includes, for example, an HMG-CoA synthetase inhibitor, an HMG-CoA reductase inhibitor, an AMPK activator such as a fibrate, a farnesyl pyrophosphate synthetase inhibitor such as a bisphosphonate, and a geranylgeranyl transferase inhibitor. Preferable protein geranylgeranylation regulator of the present invention includes an HMG-CoA reductase inhibitor, a geranylgeranyl transferase inhibitor and the like.

In consequence, as a cholesterol synthesis inhibitor or a protein geranylgeranylation regulator of the present invention, one or more agents selected from a group consisting of an HMG-CoA synthetase inhibitor, an HMG-CoA reductase inhibitor, a squalene synthetase inhibitor, a squalene epoxidase inhibitor, a lanosterol synthetase inhibitor, an AMPK activator, a farnesyl pyrophosphate synthetase inhibitor and a geranylgeranyl transferase inhibitor can be used. As the pathways of both the cholesterol biosynthesis and the geranylgeranyl pyrophosphate biosynthesis run with the same route up to the formation of farnesyl pyrophosphate, it is preferable to employ inhibitors effective to the enzymes involved in the pathway up to the farnesyl pyrophosphate formation. For example, a preferable cholesterol synthesis inhibitor or a protein geranylgeranylation regulator of the present invention includes an HMG-CoA reductase inhibitor. More preferable agent includes the statin drugs. These drugs may also be used in the form of salts or solvates thereof if needed pharmaceutically.

Examples of the preferable HMG-CoA reductase inhibitors in the present invention include, Lovastatin (chemical name: (+)-(1S,3R,7S,8S,8aR)-1,2,3,7,8,8a-hexahydro-3,7-dimethyl-8-[2-[(2R,4R)-tetrahydro-4-hydroxy-6-oxo-2H-pyran-2-yl]ethyl]-1-naphthyl(S)-2-methylbutyrate (refer to U.S. Pat. No. 4,231,938));

Simvastatin (chemical name: (+)-(1S,3R,7S,8S,8aR)-1,2,3,7,8,8a-hexahydro-3,7-dimethyl-8-[2-[(2R,4R)-tetrahydro-4-hydroxy-6-oxo-2H-pyran-2-yl]ethyl]-1-naphthyl 2,2-dimethylbutanoate (refer to U.S. Pat. No. 4,444,784));

Pravastatin (chemical name: (+)-(3R,5R)-3,5-dihydroxy-7-[(1S,2S,6S,8S,8aR)-6-hydroxy-2-methyl-8-[(S)-2-methylbutyryloxy]-1,2,6,7,8,8a-hexahydro-1-naphthyl]heptanoic acid (refer to U.S. Pat. No. 4,346,227));

Fluvastatin (chemical name: (3RS,5SR,6E)-7-[3-(4-fluorophenyl)-1-(1-methylethyl)-1H-indole-2-yl]-3,5-dihydroxy-6-heptenoic acid (refer to U.S. Pat. No. 5,354,772));

Atorvastatin (chemical name: (3R,5R)-7-[2-(4-fluorophenyl)-5-isopropyl-3-phenyl-4-phenylcarbamoyl-1H-indole-1-yl]-3,5-dihydroxyheptanoic acid (refer to U.S. Pat. No. 5,273,995));

Cerivastatin (chemical name: (3R,5S)-erythro-(E)-7-[4-(4-fluorophenyl)-2,6-diisopropyl-5-methoxymethyl-pyridine-3-yl]-3,5-dihydroxy-6-heptenoic acid (refer to U.S. Pat. No. 5,177,080));

Mevastatin (chemical name: (+)-(1S,3R,7S,8S.8aR)-1,2,3,7,8,8a-hexahydro-7-methyl-8-[2-[(2R,4R)-tetrahydro-4-hydroxy-6-oxo-2H-pyran-2-yl]ethyl]-1-naphthyl (S)-2-methylbutyrate (refer to U.S. Pat. No. 3,983,140));

Rosuvastatin (chemical name: 7-[4-(4-fluorophenyl)-6-isopropyl-2-(N-methyl-N-methanesulfonylaminopyrimidine)-5-yl]-(3R,5S)-dihydroxy-(E)-6-heptenoic acid (refer to U.S. Pat. No. 5,260,440 and JP No. 2,648,897));

Pitavastatin (chemical name: (3R,5S,6E)-7-[2-cyclopropyl-4-(4-fluorophenyl)-3-quinolyl]-3,5-dihydroxy-6-heptenoic acid (refer to U.S. Pat. No. 5,856,336, JP2,569,746));

and salts thereof. More preferable examples include Pitavastatin, Lovastatin, Simvastatin, and further more preferable example include Pitavastatin.

Examples of the preferable cholesterol synthesis inhibitor in the present invention includes an HMG-CoA reductase inhibitor, and the HMG-CoA reductase inhibitor includes a substance selected from a group consisting of lovastatin, pravastatin, simvastatin, fluvastatin, cerivastatin, atorvastatin, pitavastatin or rosuvastatin, and pharmaceutically acceptable salt thereof in each case. More preferable example of the HMG-CoA reductase inhibitor includes pitavastatin, or salt or solvate thereof.

An object of the present invention is to inhibit the activity of γ-secretase, more specifically, to inhibit the γ-secretase activity in lipid rafts. Accordingly, an agent for inhibiting the activity of γ-secretase of the present invention may be either the inhibitor of the formation of γ-secretase complex based on the inhibition of the formation of γ-secretase complex, or an agent for decreasing the distribution of an active complex of γ-secretase in lipid rafts to decrease the distribution of γ-secretase or the active complex thereof in lipid rafts.

The inhibitor of the formation of γ-secretase complex or an agent for decreasing the distribution of an active complex of γ-secretase in lipid rafts of the present invention may comprise a cholesterol synthesis inhibitor and/or a protein geranylgeranylation regulator as an active ingredient and a pharmaceutically acceptable carrier, and can be used as a pharmaceutical composition comprising these ingredients.

In addition, the present invention provides a method of treating or preventing disorder associated with the activation of γ-secretase by administration of an effective amount of the cholesterol synthesis inhibitor or the protein geranylgeraniration regulator of the present invention to a patient in need of inhibiting the γ-secretase activity. As for the patient with a disease in need of inhibition of the γ-secretase activity, the production of Aβ40, Aβ42 peptide, particularly the production of Aβ42 by the formation of an active complex of γ-secretase has to be inhibited, and such disease caused by the deposition of these peptides includes, for example, Alzheimer's disease (AD).

Administration route of a cholesterol synthesis inhibitor and/or a protein geranylgeranylation regulator of the present invention or a pharmaceutical composition of the present invention containing the same include oral administration by tablets, capsules, granules, powder, syrup and the like, or parenteral administration via intravenous injection, intramuscular injection, suppository, inhalant, transdermal absorbent, ophthalmic drops, nasal drops and the like.

For the production of such medical preparations of various dosage form, the active ingredient may be used by itself or in an appropriate combination with one or more of other pharmaceutically acceptable excipient, binding agent, extending agent, disintegrating agent, surfactant, lubricant agent, dispersing agent, buffering agent, preservative, flavoring agent, fragrance, coating agent, carrier, diluents, and the like.

In particular, for the medication with an HMG-CoA reductase inhibitor, oral administration is preferable among these administration routs. On the production of the preparation for oral administration, it is preferable to adjust pH in consideration of stability of the active ingredient (refer to JP-A-1990-6406, JP No. 2,774,037 and WO 97/23200).

Application dose of these medicines may be varied depending on factors of a patient such as body weight, age, sexuality and severity of condition of the disease. In general, however, assuming the compound represented by general formula (I) as an active ingredient, a total daily dose for an adult patient is in the range from 0.01 mg to 1000 mg, preferably 0.1 mg to 100 mg. Such dose may be given once or divided into several times a day through oral or parenteral route.

An inhibitor of γ-secretase complex formation or an agent for decreasing the distribution of an active complex of γ-secretase in lipid rafts of the present invention is an agent which inhibits substantial activity of γ-secretase by inhibiting the formation of an active complex of γ-secretase in lipid rafts or by decreasing the distribution of γ-secretase or an active complex thereof in lipid rafts, and suppress the production of Aβ40 and Aβ42 peptides, particularly the production of Aβ42. Thus, these agents are useful for treating or preventing various disorders including Alzheimer's disease (AD) caused by the disposition of these peptides.

A method of inhibiting the formation of active complex of γ-secretase or a method of modulating the distribution of an active complex of γ-secretase in lipid rafts can be conducted by adding the cholesterol synthesis inhibitor and/or the protein geranylgeranylation regulator of the present invention to a system to be treated such as cell culture or a biological system. The method of the present invention provides particularly a method of inhibiting the formation of an active complex of γ-secretase in lipid rafts or a method of decreasing the distribution of γ-secretase or an active complex thereof in lipid rafts.

The method of assaying the activity of inhibiting cholesterol synthesis of the present invention may be a method capable of assaying the amount of synthesized cholesterol, preferably a method capable of quantifying cholesterol accumulated in lipid rafts in cells. More specifically, cells are cultured in a medium containing labeled or non-labeled materials for cholesterol biosynthesis in the presence or absence of screening substance, and after predetermined period of time, an amount of cholesterol in cells particularly in the lipid rafts in cells is assayed. With respect to the labeling method, any method which can quantify without affecting the biosynthesis may be employed with no limitation, but typically labeling with an isotope is preferable. In this way, by comparison with the control, it can be determined whether the screening substance has an activity of inhibiting cholesterol synthesis. And according to the present invention, by the measurement of the inhibitory activity of the screening substance by this way, the screening of the test substance whether it has an activity of inhibiting the formation of an active complex of γ-secretase can be performed.

Also, the present invention provides a method of screening a substance which has an activity of inhibiting the formation of an active complex of γ-secretase, or a substance which has an activity to decrease the distribution of γ-secretase in lipid rafts, in which cells are cultured in the presence of the test substance and an amount of the accumulated cholesterol in lipid rafts in the cell is quantified. The procedure of quantifying accumulated cholesterol in this method may be performed by culturing cells in a medium containing labeled or unlabeled material for cholesterol synthesis in the presence or absence of a screening substance (a test substance) and measuring a content of cholesterol in the cell, particularly in lipid rafts in the cell. By this means, in comparison with the control, it can be judged whether the screening substance has an activity of inhibiting the formation of an active complex of γ-secretase or an activity of decreasing the distribution of γ-secretase in lipid rafts.

In addition, in the present invention, the method of measuring activity of inhibiting the formation of an active complex of γ-secretase, or the method of measuring activity to decrease the distribution of γ-secretase in lipid rafts includes, for example, a method of measuring the constituents of γ-secretase in lipid rafts which is previously separated from cells cultured in the presence or absence of screening substance. The practical method of separating the lipid rafts includes treatment of cells with a surfactant, or fractionation by the sucrose density-gradient method, or combined method thereof. The practical method of measuring the constituents of γ-secretase includes immunological assay of presenilin, nicastrin, APH-1 or Pen-2.

By this means, it may be judged whether the screening substance has an activity of a cholesterol synthesis inhibitor, a protein geranylgeranylation regulator or an HMG-CoA reductase inhibitor.

In the present invention, cells to be used for these screening methods are not particularly limited so long as they have lipid rafts therein and easy in culturing. Preferable cells are, for example, SH-SY5Y cell (Invitrogen) or the like.

The method of fractionating the constituents of cells of the present invention may be carried out by solubilizing the cells using proteolytic enzymes or the like, and then the cell lysate is subjected to the density-gradient separation method or the like using sucrose, cesium chloride, cesium trifluoroacetate and so on. As a biochemical fractionation method of such macro-domain, a procedure of obtaining a detergent-insoluble fraction by the sucrose density-gradient centrifugation from cell homogenate prepared in the presence of surfactant has been known, but should not be limited thereto.

Because the lipid raft is not broken through digestion by proteases, identification of lipid rafts as a specific fraction becomes possible, and detection and quantification of the constituents of an active complex of γ-secretase in the lipid rafts fraction and other fraction may be performed by the immunoblotting method and the like. In this case, as a marker for the identification of lipid rafts, flotillin may be used but should not be limited thereto.

By the method of the present invention, the distribution of each constituent of the active complex of γ-secretase in cells, more precisely, in cell membrane can be measured. By this measurement, detection and quantification of the formation of an active complex of γ-secretase may also become practical, and an activity of γ-secretase in the aforementioned cell system can be assayed.

Therefore, the screening of an effect of a test substance on γ-secretase, for example enhancing effect or inhibiting effect on the activity, can be performed by adding the test substance into a cell culture followed by measuring the distribution of the constituents of an active complex of γ-secretase in the aforementioned cell using above-described method of the present invention, and as a control, the same procedure is carried out without adding the test substance, and thus the present invention provides a new method of screening γ-secretase activity.

As the constituents required for the formation of an active complex of γ-secretase, one or more substances selected from a group consisting of nicastrin, APH-1, Pen-2 and presenilin of an active subunit of γ-secretase, preferably from a group consisting of nicastrin, APH-1 and Pen-2 may be employed.

In the present invention, cells to be used for these screening methods are not particularly limited so long as they have lipid rafts in cells and easy in culturing. Preferable cells are, for example, SH-SY5Y cell (Invitrogen) or the like.

EXAMPLES

Hereinbelow, the present invention will be specifically explained using Examples, however, the present invention should not be construed to be limited thereto.

Reference Example 1

Cell Culture
SH-SY5Y cell line (Invitrogen) was subcultured in a complete medium (DMEM (Sigma) containing 10% of fetal bovine serum (Sigma), 100 units/mL of penicillin and 100 mg/mL of streptomycin) using a dish of 15 cm diameter at 37° C.

Reference Example 2

Preparation of Detergent Insoluble Membrane Domain (Raft)

The SH-SY5Y cell was cultured in a dish of 15 cm diameter, and the cells reached confluent growth in the dish was washed with phosphate buffered saline (PBS). The cells were detached from the dish using cell scraper and recovered in PBS, then centrifuged at 9807 m/s$^2$ for 5 minutes. The precipitated cells were suspended in buffer R (20 mM Tris-HCl pH 7.6, 150 mM NaCl, 1 mM EDTA) containing 200 μL of a mixture of 2% CHAPSO and proteases (Complete protease mixture) (Roche). Solubilization of the cell was performed by means of leaving the cell suspension for standing on an ice bath for 20 minutes. After solubilizing, 800 μL of the buffer R containing 56.25% sucrose was added to make the final concentration to be 45% sucrose and 0.4% CHAPSO, and placed in the bottom of centrifuging tube. Further, 3 mL of the buffer R containing 35% sucrose and 1 mL of the buffer R containing 5% sucrose were overlaid sequentially on top of the layers. After centrifugation at 980700 m/s$^2$ (32000 rpm) for 16 hours at 4° C. using Beckman ultracentrifuge equipped with SW55 rotor, each 500 μL aliquot was withdrawn from top as fractions.

Reference Example 3

SDS-Polyacrylamide Gel Electrophoresis and Immunoblotting

After SDS-polyacrylamide gel electrophoresis was carried out for each fraction obtained in the Reference Example 2, immunoblotting was performed. The antibodies used were nicastrin N-19 (Santa Cruz) as a nicastrin recognizing antibody, anti-G1L3 as an antibody recognizing C-terminal region of presenilin 1, anti-G2L as an antibody recognizing C-terminal region of presenilin 2, anti-PNT3 as a PEN-2 recognizing antibody, Flotillin-1 (BD Sciences) as a flotillin-1 recognizing antibody, and Calnexin (BD Biosciences) as a calnexin recognizing antibody.

After reacting at room temperature for 1 hour or at 4° C. overnight, the gels were washed twice with TBS-Tween (20 mM Tris-buffered saline, pH 7.4, 0.05% Tween 20). Then, the gels were reacted with HRP-conjugated anti mouse IgG antibody, anti goat IgG antibody, or anti rabbit IgG antibody each for 1 hour, and washed with TBS-Tween. And then, an X-ray film was exposed to the chemiluminescence generated using SuperSignal West Dura (Pierce).

Example 1

Treatment by methyl-β-cyclodextrin (refer to FIG. 1 and FIG. 2)

The SH-SY5Y cell was cultured in a dish of 15 cm diameter, and the cells reached confluent growth in the dish were washed with PBS. After that, methyl-β-cyclodextrin (Sigma) dissolved in DMEM to make the final concentration to be 0 to 2 mM was added to the dish, and cultured at 37° C. for another 30 minutes. These cells were processed and fractionated according to the method described in the Reference Example 2, and subjected to the immunoblotting.

The results were shown in FIG. 1. Also the results of quantification of cholesterol and protein content were shown by graph in FIG. 2. Numeric symbols of 1 to 10 in FIG. 1 and FIG. 2 indicate fraction number of the cell, and lipid rafts is in the fraction number 3.

FIG. 1 shows the results of immunoblotting of cell membrane fractions after treatment with methyl-β-cyclodextrin (MβCD). Numeric symbols from 1 to 10 in FIG. 1 are the fractionation numbers of sucrose density-gradient centrifugation of cell homogenate; the substances with low specific gravity come up and appear in the earlier fractions. As a marker substance, flotillin-1 was utilized (refer to FIG. 1E). FIG. 1A illustrates nicastrin; FIG. 1B illustrates presenilin-1 (PS1) of an active subunit of γ-secretase; FIG. 1C illustrates presenilin-2 (PS2); FIG. 1D illustrates PEN-2; and FIG. 1E illustrates flotillin-1 as a marker substance of lipid rafts. In PS1 and PS2 of FIG. 1B and FIG. 1C respectively, "CTF" means "carboxy terminal fragment" indicating that the immunoblotting was carried out using corresponding antibody specific for each C-terminal region of PS1 or PS2. Each figure of immunoblotting is shown in the order of methyl-β-cyclodextrin concentration of 0 mM, 1 mM and 2 mM, from the top.

FIG. 2 shows a graph of the changes of cholesterol and protein content in the cell membrane fractions by methyl-β-cyclodextrin treatment. As the results, cholesterol was removed from lipid rafts (fraction 3) by methyl-β-cyclodextrin treatment (outline symbols in FIG. 2) and flotillin as a marker protein of lipid rafts was moved from the original position of the lipid rafts of fraction 3 to fraction 9 and 10 (refer to FIG. 1E). In the same way, the constituents of γ-secretase such as nicastrin, presenilin-1, presenilin-2 and Pen-2 have disappeared from lipid rafts fraction (fraction 3) (refer to FIG. 1A, FIG. 1B, FIG. 1C and FIG. 1D). Thus, it was confirmed that methyl-β-cyclodextrin destroyed the raft structure by withdrawing cholesterol from lipid rafts and inhibited the formation of an active complex of γ-secretase in lipid rafts.

Example 2

Figure 3A:
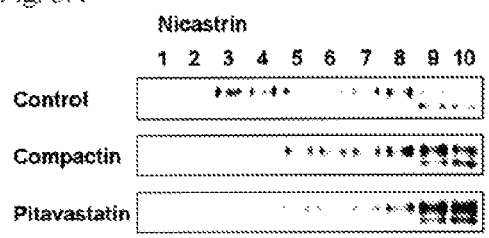
FIG. 3A illustrates the results for nicastrin.
Figure 3C:
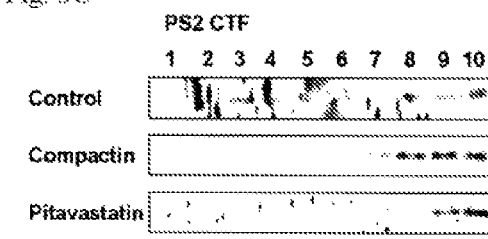
FIG. 3C illustrates for PS2CTF.
Figure 3B:
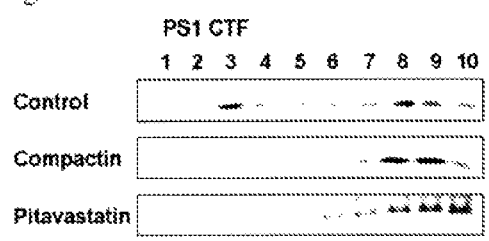
FIG. 3B illustrates for PS1CTF.
Figure 3D:
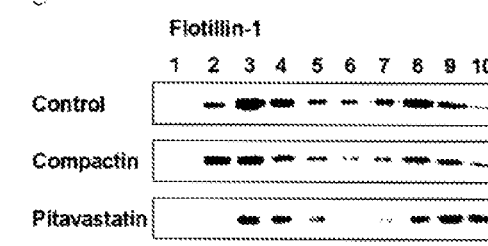
FIG. 3D illustrates for flotillin-1. Each drawing of immunoblotting corresponds to the results for control, addition of 50 μM compactin and addition of 5 μM pitavastatin, respectively, from the top.
Figure 4:
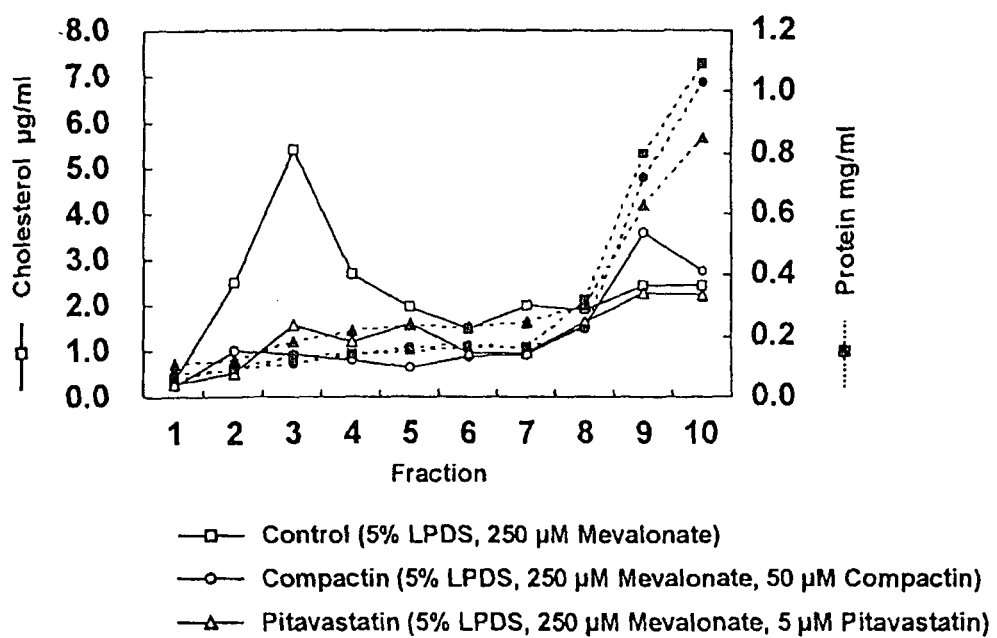
FIG. 4 shows a graphic representation of the changes of cholesterol and protein contents in the cell membrane fractions after treatment with HMG-CoA reductase inhibitor. Square symbols (□ and ■) indicate the case of the addition of 250 μM of mevalonic acid as a control; circle symbols (○ and ●) indicate the case of compactin (250 μM of mevalonic acid plus 50 μM of compactin); and triangle symbols (Δ and ▲) indicate the case of pitavastatin (250 μM of mevalonic acid plus 5 μM of pitavastatin). Outline symbols indicate cholesterol content and black symbols indicate protein content. The horizontal axis of the graph indicates fraction number, the vertical axis on the left hand indicates cholesterol concentration (μg/mL), and the vertical axis on the right hand indicates protein concentration (mg/mL).

Treatment by the Treatment of an HMG-CoA Reductase Inhibitor (Refer to FIG. 3 and FIG. 4)

The SH-SY5Y cell was cultured in a dish of 15 cm diameter and the cells of just before arriving confluent growth in a dish were washed with PBS. After that, the cells were cultured in DMEM containing 5% of LPDS, 250 μM of mevalonic acid and 50 μM of compactin or 5 μM of pitavastatin as a cholesterol synthesis inhibitor for 48 hours. These cells were processed and fractionated according to the method described in the Reference Example 2, and subjected to the immunoblotting.

The results were shown in FIG. 3. Also the results of quantifications of cholesterol and protein content were shown by graph in FIG. 4. Numeric symbols of 1 to 10 in FIG. 3 and FIG. 4 indicate fraction numbers of the cell, and lipid rafts is in the fraction number 3. FIG. 3 shows the results of immunoblotting of cell membrane fractions after treatment with an HMG-CoA reductase inhibitor. FIG. 3A illustrates nicastrin; FIG. 3B illustrates CTF of PS1; FIG. 3C illustrates CTF of PS2; FIG. 3D illustrates flotillin-1. Each figure of immunoblotting is shown in the order from the top; control, namely no addition of an HMG-CoA reductase inhibitor; mid-position, addition of 50 compactin; lower position, addition of 5 μM pitavastatin.

FIG. 4 shows a graph of the changes of cholesterol and protein content in the cell membrane fractions by an HMG-CoA reductase inhibitor. Square symbols (□ and ■) indicate the case of the addition of 250 μM of mevalonic acid as a control; circle symbols (○ and ●) indicate the case of compactin (250 μM of mevalonic acid plus 50 μM of compactin); and triangle symbols (Δ and ▲) indicate the case of pitavastatin (250 μM of mevalonic acid plus 5 μM of pitavastatin). Outline symbols indicate cholesterol contents and black symbols indicate protein contents.

As the results, by the effect of compactin and pitavastatin as an HMG-CoA reductase inhibitor, cholesterol content in lipid rafts (fraction 3) was decreased (refer to FIG. 3), and similarly as shown in Example 1, the constituents of γ-secretase such as nicastrin, presenilin-1 and presenilin-2 have disappeared from lipid rafts fraction (fraction 3) (refer to FIG. 3A, FIG. 3B and FIG. 3C). Thus, it was confirmed that compactin and pitavastatin inhibited the formation of an active complex of γ-secretase in lipid rafts, while flotillin still remained in the lipid rafts fraction, indicating that the structure of lipid rafts was kept unchanged.

Industrial Applicability

The present invention provides a pharmaceutical composition which inhibits the formation of an active complex of γ-secretase and thereby suppresses the productions of Aβ40 and Aβ42 peptides, particularly the production of Aβ42 peptide. Therefore, it is useful for treatment or prevention of various disorders caused by the deposition of these peptides such as Alzheimer's disease (AD), and thus, the present invention has industrial applicability. In addition, the present invention provides a method of screening a substance having an effect of inhibiting the formation of an active complex of γ-secretase or a method of screening a substance having an effect of decreasing the distribution of γ-secretase in lipid rafts. And therefore, the present invention provides a method of searching for an active ingredient of a useful medical drug by simple procedure. Thus, the present invention has industrial applicability.

The invention claimed is:

1. A method of screening for a test substance which decreases the amount of active complex of γ-secretase in a lipid raft, comprising:
    preparing cells in two or more dishes,
    adding the test substance to one of said dishes,
    culturing cells in each of said dishes,
    detecting or quantifying constituents required by γ-secretase for the formation of an active complex thereof in a lipid raft fraction of the cultured cells in each of said dishes,
    detecting or quantifying a constituent indicative of intact lipid rafts in a lipid raft fraction of the cultured cells in each of said dishes, and
    determining that the test substance is a substance which decreases the amount of active complex of γ-secretase in a lipid raft without destroying the structure of the lipid raft if (i) the constituents required by γ-secretase for the formation of an active complex thereof decrease in the lipid raft fraction of the cultured cells in a dish into which the test substance is added, as compared to a dish into which the test substance was not added and (ii) if the constituent indicative of intact lipid rafts is present in the lipid raft fraction of the cultured cells in the dish into which the test substance was added.

2. The method according to claim 1, wherein the constituents required for the formation of an active complex of γ-secretase are one or more kinds of substances selected from a group consisting of nicastrin, presenilin-1 and presenilin-2.

3. The method according to claim 1, wherein the constituent indicative of intact lipid rafts is flotillin-1.

4. The method according to claim 1, wherein the constituents required for the formation of an active complex of γ-secretase are at least two kinds of substances selected from a group consisting of nicastrin, presenilin-1 and presenilin-2.

5. The method according to claim 1, wherein the constituents required for the formation of an active complex of γ-secretase are nicastrin, presenilin-1 and presenilin-2.

\* \* \* \* \*